(12) United States Patent
Sotos et al.

(10) Patent No.: US 8,037,886 B2
(45) Date of Patent: Oct. 18, 2011

(54) SYSTEM AND METHOD FOR TREATMENT OF UPPER AIRWAY DISORDERS

(76) Inventors: John George Sotos, Palo Alto, CA (US); John Leyon Branscum, Belmont, CA (US)

( * ) Notice: Subject to any disclaimer, the term of this patent is extended or adjusted under 35 U.S.C. 154(b) by 217 days.

(21) Appl. No.: 12/506,197

(22) Filed: Jul. 20, 2009

(65) Prior Publication Data

US 2010/0217426 A1 Aug. 26, 2010

Related U.S. Application Data

(62) Division of application No. 11/077,796, filed on Mar. 10, 2005, now abandoned.

(60) Provisional application No. 60/551,723, filed on Mar. 10, 2004.

(51) Int. Cl.
*A61F 5/56* (2006.01)
(52) U.S. Cl. .................. 128/848; 128/859; 602/902
(58) Field of Classification Search ............ 128/848, 128/859, 861, 862; 602/902; 433/6
See application file for complete search history.

(56) References Cited

U.S. PATENT DOCUMENTS

| | | | | | |
|---|---|---|---|---|---|
| 5,313,960 | A | * | 5/1994 | Tomasi | 128/848 |
| 5,365,945 | A | * | 11/1994 | Halstrom | 128/848 |
| 5,562,106 | A | * | 10/1996 | Heeke et al. | 128/848 |
| 5,947,724 | A | * | 9/1999 | Frantz et al. | 433/19 |
| 5,950,624 | A | * | 9/1999 | Hart | 128/207.15 |
| 6,161,542 | A | * | 12/2000 | Halstrom | 128/848 |
| 6,464,924 | B1 | * | 10/2002 | Thornton | 264/331.12 |

* cited by examiner

*Primary Examiner* — Steven O Douglas

(57) ABSTRACT

The present invention provides a system for treating a mammalian patient having obstructive sleep disordered breathing, e.g., sleep apnea. The system has a set of appliances including a first appliance being adapted to displace a mandible of the patient by a first predetermined geometry relative to a maxilla of the patient. The set also includes at least a second appliance adapted to displace the mandible of the patient by a second predetermined geometry relative to the maxilla of the patient. In a specific embodiment, the first predetermined geometry is substantially different from the second predetermined geometry. Preferably, either one of the first appliance or at least the second appliance is worn by the patient based upon a predetermined treatment plan that includes one or more provisions for wearing at least the first and the second appliances.

7 Claims, 8 Drawing Sheets

FIGURE #1
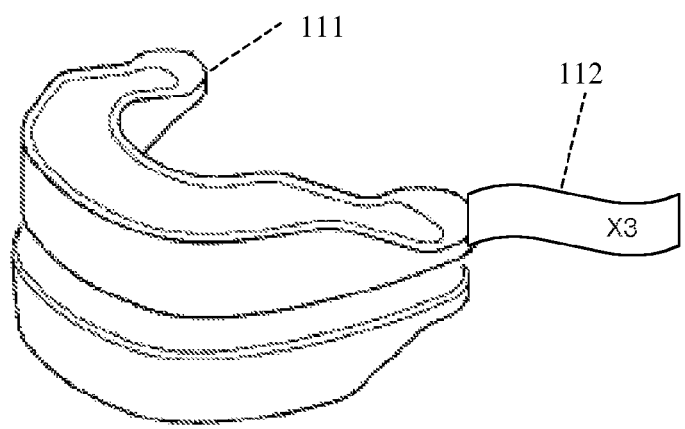
FIGURE #1-A
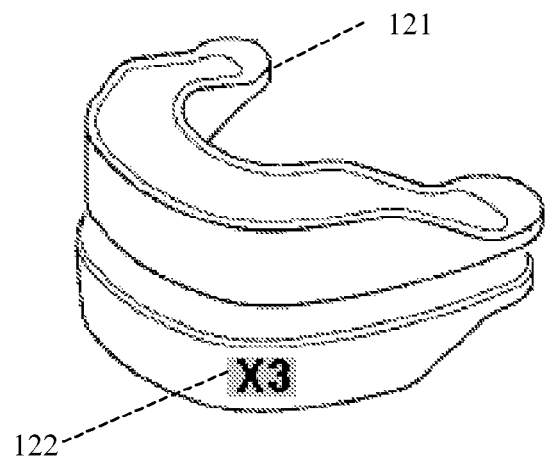
FIGURE #1-B

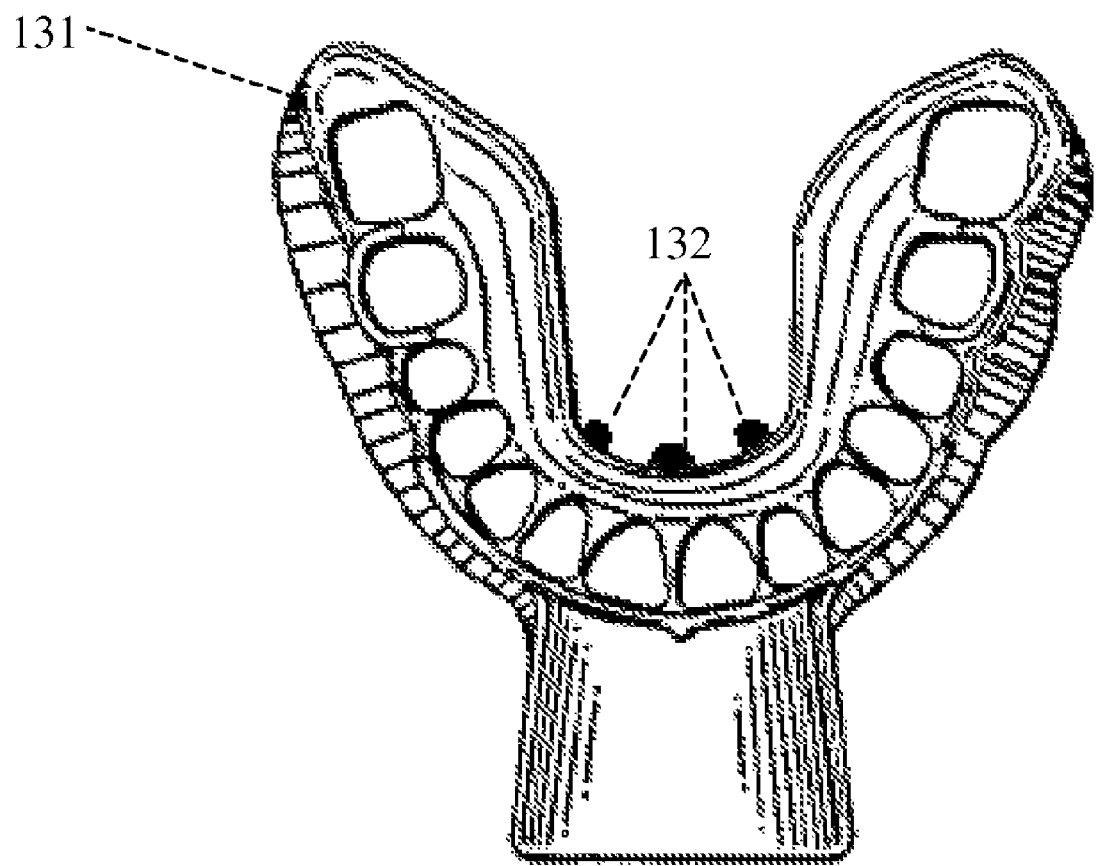
FIGURE #1-C

FIGURE #2
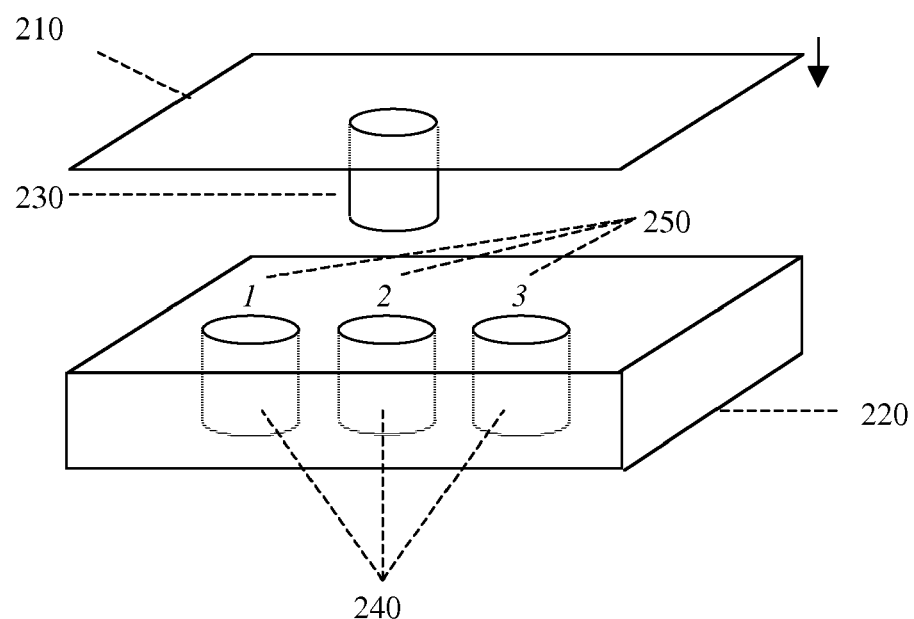

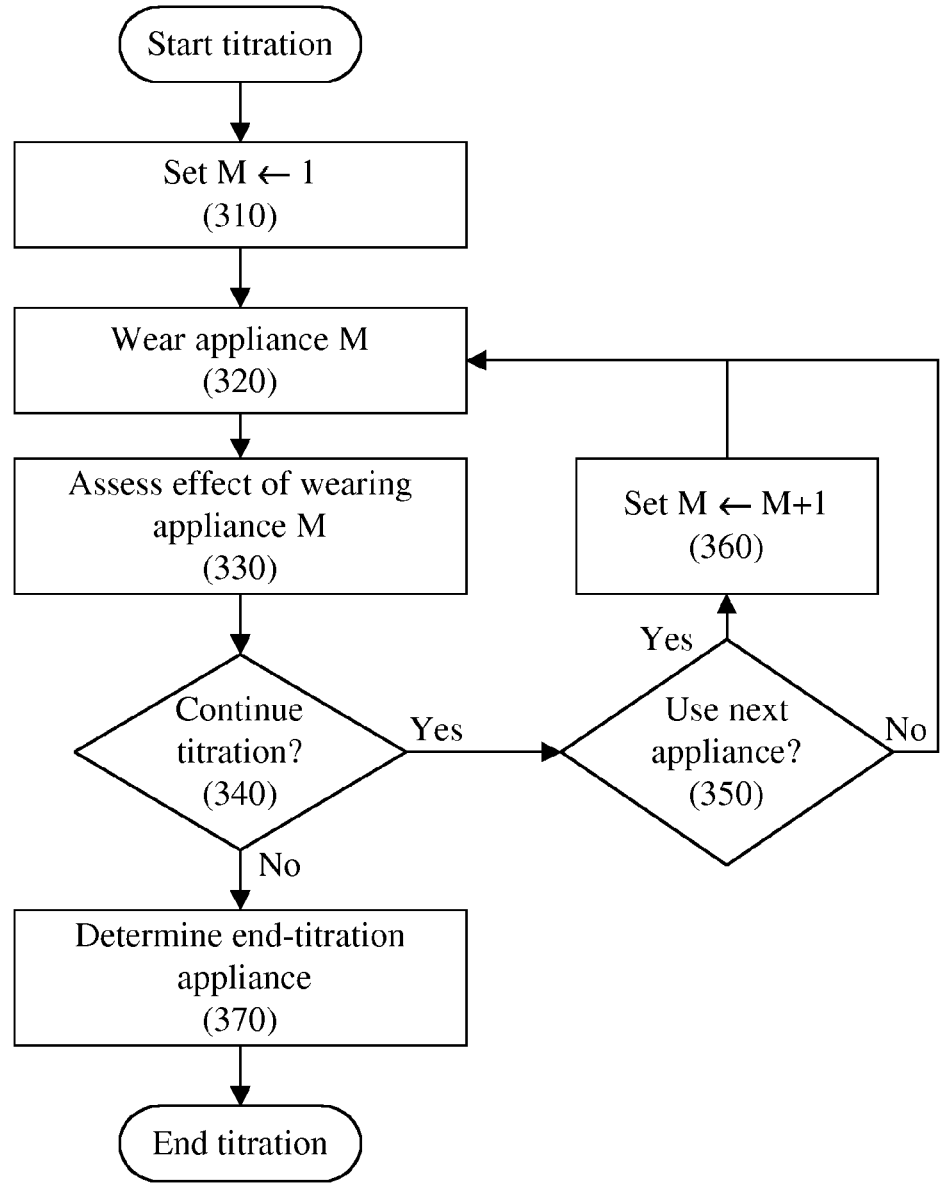

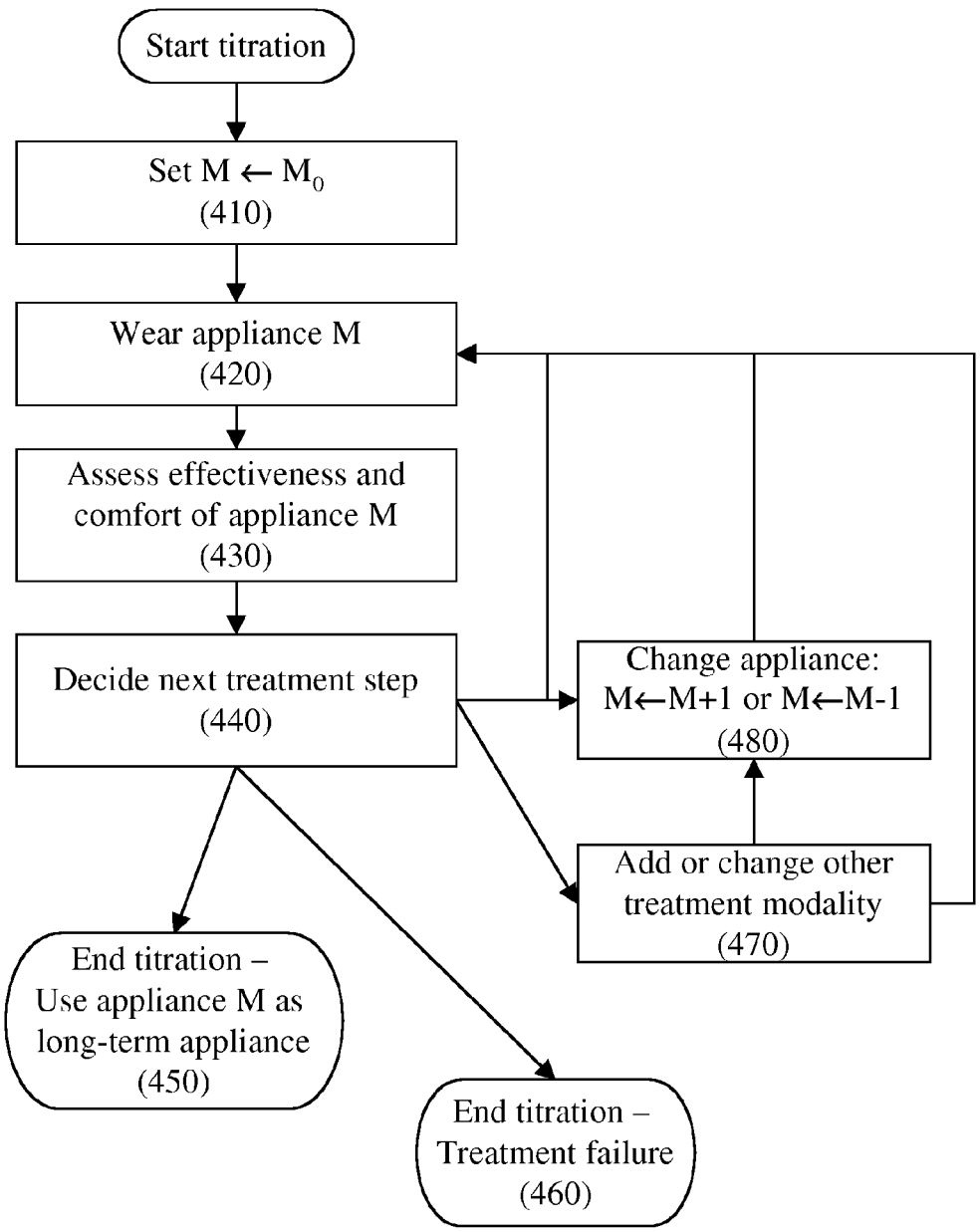

Fig. #5

|  |  | Effectiveness | | | |
|---|---|---|---|---|---|
|  |  | 0 | 1 | 2 | 3 |
| Discomfort | 0 | Appliance M ←M+1 | Appliance M ←M+1 | Appliance M ←M+1 | Titration done. Use appliance M in long term. |
|  | 1 | Wear appliance M for one week. Then M ← M+1 | Wear appliance M for one week. Then M ← M+1 | Wear appliance M for one week. Then M ← M+1 | If appliance M-1 has not been tried: M ←M-1. Else use appliance M or M-1 long term. |
|  | 2 | Treatment failure. | Add or increase additional treatment modality. | Appliance M ←M-1 | Appliance M ←M-1 |

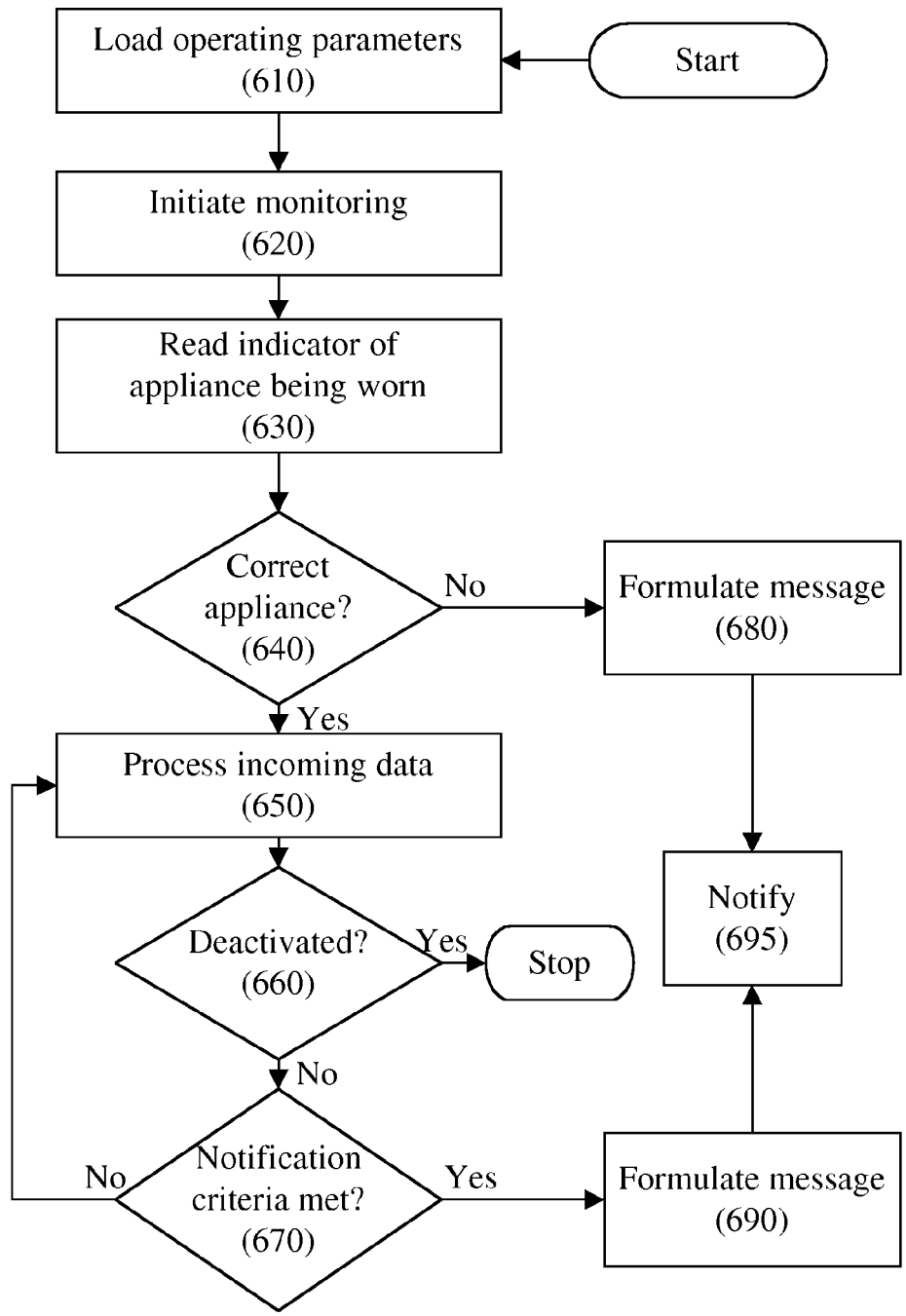

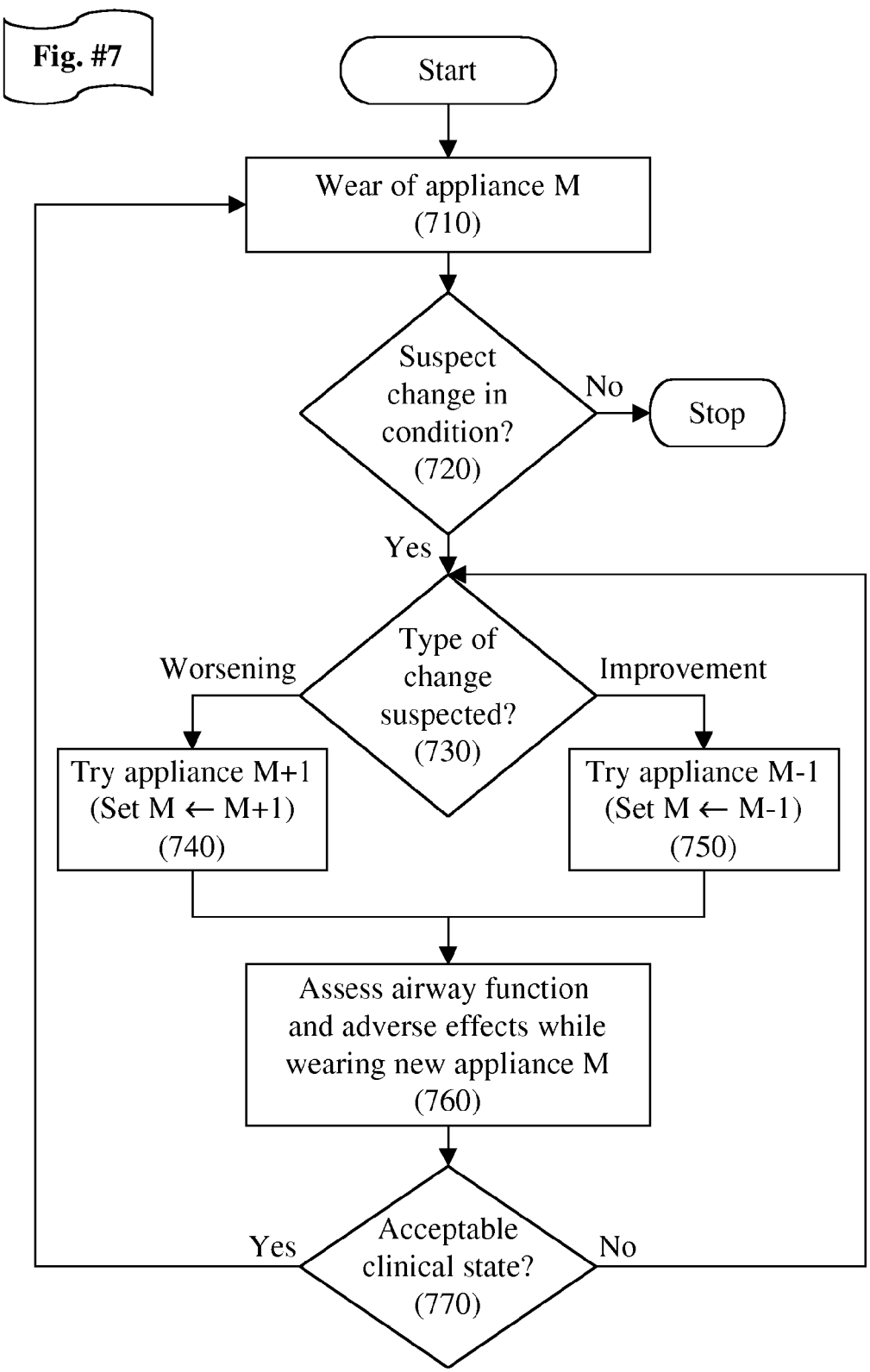

SYSTEM AND METHOD FOR TREATMENT OF UPPER AIRWAY DISORDERS

CROSS-REFERENCES TO RELATED APPLICATIONS

This application is a divisional of U.S. patent application Ser. No. 11/077,796 filed Mar. 10, 2005 now abandoned. This application claims priority to U.S. Provisional Patent No. 60/551,723 filed Mar. 10, 2004, commonly assigned, and hereby incorporated by reference for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention generally relates to ways of treating health related disorders. More particularly, the invention provides a system and method for treating certain types of breathing problems occurring in a mammal during sleep or other states of diminished consciousness. Merely by way of example, the invention is applied using a plurality of oral appliances for stepped treatment of obstructive sleep disordered breathing.

Many dentists employ oral appliances to treat various forms of obstructive sleep disordered breathing (OSDB). In this context, Schmidt-Nowara et al al (Sleep. 1995 July; 18(6):501-10.) define "oral appliances" as a generic term for "devices inserted into the mouth in order to modify the position of the mandible, the tongue, and other structures in the upper airway for the purpose of relieving snoring or sleep apnea." Lowe (Pages 929-939 in: M H Kryger et al (eds). Principles and Practice of Sleep Medicine. 3rd edition. Philadelphia: W.B. Saunders Company, 2000.) (Oral Maxillofacial Surg Clin N America. 2002; 14:305-317.) describes several commercially available oral appliances. These devices are generally worn by patients during sleep, and removed after awakening.

As implied by its name, obstructive sleep disordered breathing is generally associated with an obstruction to respiratory airflow during sleep. Kuna and Remmers (Pages 840-858 in: M H Kryger et al (eds). Principles and Practice of Sleep Medicine. 3rd edition. Philadelphia: W.B. Saunders Company, 2000.) declare "The site of upper airway obstruction lies in the pharynx," which is a component of the upper airway. Ferguson (Clin Chest Medicine. 2003; 24:355-364.) states that "Oral appliances may improve upper airway patency by enlarging the upper airway or decreasing upper airway collapsibility." She further notes that that simple active anterior movement of the tongue or mandible can increase cross-sectional airway size. Lowe (Oral Maxillofacial Surg Clin N America. 2002; 14:305-317.) notes that the tongue is attached to the mandible and that devices that move the mandible anteriorly generally move the tongue anteriorly as well. He discusses the therapeutic mechanism(s) of oral appliances: "Oral appliances . . . appear to work because of an increase in airway space, the provision of a stable anterior position of the mandible, advancement of the tongue or soft palate, and possibly by a change in genioglossus muscle activity." Guilleminault and Quo (Dent Clin North Am. 2001 October; 45(4):643-656.) note that different mechanisms may contribute in children: mandibular forward-repositioning functional appliances "achieve results on the combined premise of growth adaptation and tooth movement."

Ferguson (Clin Chest Medicine. 2003; 24:355-364.) reviews several studies of the effectiveness of oral appliance therapy for OSDB and concludes they are effective in some patients with OSDB, particularly those with less severe OSA or simple snoring. She remarks that oral appliances are an appealing form of therapy for OSDB "because they are simple to use, reversible, and portable and generally have a low complication rate."

According to Ferguson (Clin Chest Medicine. 2003; 24:355-364.) the two major types of oral appliances used in treating OSDB are tongue repositioning devices and mandibular repositioning appliances (MRAs). Schmidt-Nowara et al (supra.) state that "all oral appliances produce downward rotation of the mandible to varying extent; many also advance the mandible by design."

Ivanhoe and Attanasio (Dent Clin North Am. 2001 October; 45(4):733-58.) report evidence that a compromised airway, as may be encountered in OSDB, "can be almost completely restored" by moving the mandible forward to 100% of its protrusive capability. On the other hand, they also report that positioning the mandible at 100% of its protrusive capability is "not an acceptable position for most patients because it is generally uncomfortable to maintain through the entire course of sleeping."

From this, one might conclude, as a rule of thumb, the greater the degree of mandibular advancement conferred by an MRA, the more effective it is in treating OSDB, all other factors being equal. As a further rule of thumb, however, the greater the degree of mandibular advancement, the greater the likelihood the patient will experience discomfort, all other factors being equal.

According to Lowe (Pages 929-939 in: M H Kryger et al (eds). Principles and Practice of Sleep Medicine. 3rd edition. Philadelphia: W.B. Saunders Company, 2000.), "dentists early on realized that determining the correct jaw position was the most difficult step in using oral appliances successfully" in treating OSDB. In many cases there is a tradeoff between efficacy and comfort.

To ease the task of determining the correct jaw position, the dentist may employ an adjustable MRA, as distinguished from a non-adjustable MRA. According to Schmidt-Nowara et al (Sleep. 1995 July; 18(6):501-10), adjustable MRAs allow readjustment of the mandibular position after initial construction of the device; for non-adjustable MRAs, such readjustments would require refabrication of the entire device. Cartwright (Sleep Med Rev. 2001 February; 5(1):25-32), for example, views the lack of adjustability in an oral appliance as disadvantageous.

According to one method of using an adjustable MRA, anterior displacement of the mandible is gradually increased (via the MRA) over time, until the desired therapeutic effect is attained or until patient discomfort supervenes. Exemplary adjustment rates include 0.25 mm/night (Ivanhoe and Attanasio. Dent Clin North Am. 2001 October; 45(4):733-58), 0.5 mm/week (Lowe. Oral Maxillofacial Surg Clin N America. 2002; 14:305-317), and 1.5 mm increments (Lowe 2002 supra.). Ivanhoe and Attanasio (supra.) report that, with either a fixed or adjustable MRA, "the initial position of the mandible is generally approximately 70% to 75% of maximum protrusion relative to maximum retrusion." After initial fitting, an adjustable MRA may be configured by repeated assessment to yield the best tradeoff between efficacy and comfort, a process sometimes called "titration."

A variety of mechanisms, e.g. a screw as used in one MRA known as the Klearway device, or a plunger mechanism as used in the Herbst appliance, have been used to confer adjustability on MRAs. Some mechanisms allow the patient to make adjustments to the MRA. Other mechanisms are less likely to be configured by the patient, and are more commonly adjusted by the dentist. In either case, problems may be associated with adjustable appliances.

For MRAs that are adjusted by the dentist, each adjustment will normally require the patient to bring the MRA to the dentist's office for the adjustment. Such repeated trips may be inconvenient for the patient.

For MRAs that are adjusted by the patient, care must be taken to ensure the instructions to the patient are clear and correctly understood, and that the proper adjustment tools, if any, are available. Oversight by the dentist may also be necessary to detect errors in adjustment by the patient. For example, if the patient turns the screw of the Klearway device in one direction, the effect will be to advance the mandible; if turned in the other direction, the effect will be opposite. Furthermore, a special tool is given to the patient to make adjustments in the Klearway; the patient may lose this tool. Lowe (Oral Maxillofacial Surg Clin N America. 2002; 14:305-317.) cautions that disengaging the tool from the Klearway at the wrong time may prevent the patient from fully engaging the tool at a later time. Some patients with mental impairment or poor hand-eye skills, perhaps due to poor eyesight or severe arthritis, may be unable to adjust the appliance correctly. Thus, it is reasonable to expect that at least some patients tasked to adjust a MRA will have to be seen in a dentist's office at some point during the titration process.

Some adjustable appliances have the potential disadvantage of requiring concentration to make adjustments. For example, an appliance requiring the turn of a screw cannot be adjusted without attention to the screw, the method of turning the screw, and so forth. This may limit the situations in which the appliance may be adjusted, and increase the difficulty that certain classes of patients, may have with the appliance.

Some patients may have to be seen in a dentist's office at the conclusion of the titration process, even when the adjustments have gone smoothly. Advice on the Klearway device, for example, recommends that the dentist "lock in" the configuration of the device once it has been properly adjusted, as follows (Lowe. Oral Maxillofacial Surg Clin N America. 2002; 14:305-317): "The expansion screw should be tied off with stainless steel ligature wire or filled in with cold cure acrylic to prevent any further movement of the screw." An appliance thus locked-in may no longer be adjustable. Non-adjustability may become undesirable later, as Ivanhoe and Attanasio (Dent Clin North Am. 2001 October; 45(4):733-58.) caution that "titration may become necessary again at some future time if sleep disorder symptoms recur or tooth or temporomandibular joint sensitivity appears."

Another potential disadvantage of adjustable MRAs is their mechanical complexity. Mechanical complexity may cause increased manufacturing expense and/or increased failure rates. The adjustment mechanism in the Klearway device, for example, appears to be a component that must itself be manufactured separately and integrated into the rest of the device. It is also a component that may fail. In 2001 Cartwright (Sleep Med Rev. 2001 February; 5(1):25-32.) quoted a typical cost of $40-400 for certain types of non-adjustable oral appliances used to treat OSDB, and compared this to a typical $800-2000 cost for an adjustable MRA.

Thus, it is seen that MRAs may have a variety of potential shortcomings, including being non-adjustable, inconvenient, difficult or confusing for patients to adjust, relatively failure-prone, and expensive. Adjustable appliances rendered non-adjustable at the completion of titration may not be able to be used if re-titration becomes necessary or desirable.

From the above, it is desirable to have improved techniques for treating health related disorders.

BRIEF SUMMARY OF THE INVENTION

According to the invention, techniques including a system and method for treating certain types of breathing problems occurring in a mammal during sleep and/or other states of diminished consciousness are provided. More specifically, the invention relates to a system and method for stepped treatment of obstructive sleep disordered breathing, using a plurality of oral appliances.

In a specific embodiment, the present invention provides a system for treating a patient having obstructive sleep disordered breathing, e.g., sleep apnea. The system has a set of appliances including a first appliance being adapted to displace a mandible of the patient by a first predetermined geometry relative to a maxilla of the patient. The set also includes at least a second appliance adapted to displace the mandible of the patient by a second predetermined geometry relative to the maxilla of the patient. In a specific embodiment, the first predetermined geometry is substantially different from the second predetermined geometry. Preferably, either one of the first appliance or at least the second appliance is worn by the patient based upon a predetermined treatment plan that includes one or more provisions for wearing at least the first and the second appliances.

In an alternative specific embodiment, the present invention provides a method for treating a patient having obstructive sleep disordered breathing. The method comprises selecting an appliance from a set of appliances. The set of appliances is adapted to displace a mandible of the patient by a plurality of predetermined geometries relative to a maxilla of the patient, the set of appliances comprising a first appliance being adapted to displace the mandible by a first predetermined geometry relative to the maxilla, at least a second appliance adapted to displace the mandible by a second predetermined geometry relative to the maxilla, and the first predetermined geometry is substantially different from the second predetermined geometry. The method further comprises inserting the selected appliance into an oral cavity of the patient, maintaining the selected appliance in the oral cavity during a first time period associated with a first period of sleep and repeating the selecting, inserting, and maintaining during a second time period associated with a second period of sleep for either the first appliance or the second appliance based upon if the first appliance or the second appliance was previously selected, inserted, and maintained; and a predetermined treatment plan that includes one or more provisions for wearing at least the first and the second appliances.

In an alternate specific embodiment the present invention provides a method for fabricating a set of appliances for treating a patient having obstructive sleep disordered breathing. The method comprises obtaining information associated with a mechanical description of the patient's oral cavity, manufacturing a set of appliances, packaging the set of appliances, and transmitting the set of appliances to the patient. In a specific embodiment, the set of appliances is adapted to displace a mandible of the patient by a plurality of predetermined geometries relative to a maxilla of the patient. The set of appliances comprises a first appliance being adapted to displace the mandible by a first predetermined geometry relative to the maxilla, at least a second appliance adapted to displace the mandible by a second predetermined geometry relative to the maxilla, and the first predetermined geometry is substantially different from the second predetermined geometry. The transmitting of the set of appliances includes the first appliance and at least the second appliance.

Various additional objects, features, and advantages of the present invention can be more fully appreciated with reference to the detailed description and accompanying drawings that follow.

BRIEF DESCRIPTION OF THE DRAWINGS

FIGS. #1A-1C show appliances and appliance indicators according to an embodiment of the present invention.

FIG. #2 shows a portion of an appliance, wherein one indicator is selected from a plurality of possible indicators by virtue of the configuration of the appliance, according to an embodiment of the present invention.

FIG. #3 shows a flowchart of a portion of a treatment plan according to an embodiment of the present invention.

FIG. #4 shows a flowchart of a portion of an alternative treatment plan according to an embodiment of the present invention.

FIG. #5 shows a table for deciding what the next treatment should be in a treatment plan according to an embodiment of the present invention.

FIG. #6 shows a method of operation for an assessment means during rapid titration according to an embodiment of the present invention.

FIG. #7 shows a flowchart of a portion of a re-titration treatment plan according to an embodiment of the present invention.

DESCRIPTION OF THE SPECIFIC EMBODIMENT

According to the present invention, techniques for treating health related disorders are provided. More particularly, the present invention provides improved methods and systems for treating a subset of disorders in which (a) the physical configuration of the upper airway produces, or threatens to produce, adverse consequences related to respiration, and (b) positioning oral structure(s) such as the mandible and/or tongue lessens or eliminates the adverse consequences. The subset of disorders includes, but is not limited to, obstructive types of sleep disordered breathing (OSDB). Other conditions of diminished consciousness, e.g. coma, stupor, the anesthetic state, and the near-term post-anesthetic state, may also be associated with physical configurations of the upper airway that impede, or threaten to impede, ventilation.

Because a patient who had anesthesia in, for example, 1968, is still, strictly speaking, in a post-anesthetic state today, we use the phrase "near-term post-anesthetic state" to refer to a state of the patient relatively soon after the administration of anesthesia, during which the anesthetic or its metabolites are having a physiological effect on the patient.

Obstructive sleep disordered breathing includes conditions such as obstructive sleep apnea (OSA), the upper airway resistance syndrome (UARS), and snoring. Persons having obstructive apneas, obstructive hypopneas, or high resistance breathing (culminating, in classic UARS, in a respiratory effort related arousal) at rates below the diagnostic threshold for OSA and UARS may also be said to have a type of OSDB.

Continuous positive airway pressure (CPAP) has been reported as successful in treating some patients with central sleep apnea (CSA) (Javaheri. Clin Chest Med. 2003; 24:207-222.). CPAP is generally known as a treatment for OSDB. Thus, because it appears that at least one treatment directed at the physical configuration of the upper airway (CPAP) may be helpful in the treatment of CSA, it is reasonable to hypothesize that another such treatment (oral appliances) may also benefit some patients with CSA. We therefore note that the present invention may find use in the treatment of CSA or in "mixed apnea" (i.e. a combination of CSA and OSDB). For conceptual clarity, we will usually refer to use of the invention in treating only OSDB, but this should not be taken as a limitation of the invention's possible uses. Furthermore, we consider mixed sleep apnea as a type of OSDB, in which CSA is an additional characteristic.

Thus, herein we generalize the spectrum of conditions amenable to oral appliance therapy beyond those mentioned by Schmidt-Nowara et al (Sleep. 1995 July; 18(6):501-10).

In the present invention, treatment is accomplished with a plurality of oral appliances, each of which may (a) constrain the positions that certain oral structures may take with respect to certain other oral structures in order to achieve a therapeutic effect on a mammalian patient's airway and/or (b) prepare the patient for subsequent use of an appliance that does a positioning as in (a). For example, in case (b), a patient may not be able to immediately tolerate an appliance that puts his or her mandible into a therapeutic position, and so one or more appliances without a therapeutic effect on the airway may be worn by the patient to gradually accustom him or her to increasing mandibular displacement, until the therapeutic appliance may be tolerated.

The present invention is not limited to a specific type of appliance. Merely by way of example, the invention provides for appliances implemented as mandibular repositioning appliances, as tongue positioning devices, and as other types of devices. Tongue repositioning devices reposition the tongue with respect to the mandible (as opposed to MRAs, where the mandible is repositioned with respect to the maxilla).

Merely by way of example, MRAs constrain the positions a patient's mandible may take with respect to the patient's maxilla. By "maxilla," we also include generally fixed maxillary structures, such as teeth. We call the union of all possible mandibular positions allowed by a properly worn appliance of this type the "geometry" of the appliance. The geometry of other types of appliances, e.g. tongue retaining appliances, may be defined similarly, but with reference to other oral structures.

Appliance geometries have an abstract shape and location, i.e. they may often be conceptualized as a three-dimensional (or less) object located in a three-dimensional coordinate space. For an MRA, the coordinate space is typically referenced to the maxilla or to a neutral position of the mandible, and one can generally conceptualize the appliance's geometry as the volume of space swept out by a fixed point on the mandible as the mandible moves through all possible positions allowed by the appliance.

Some oral appliances tightly constrain the position of certain oral structures while others allow movement leeway. For example, an MRA that does not permit any mandibular movement has a geometry approximating a single point, corresponding to the single position the mandible can assume. By contrast, an MRA that allows some motion of the mandible can, in principle, have a geometry approximating one-, two-, or three-dimensional shapes, depending on how many degrees of movement freedom the mandible is permitted. Some MRAs, for example, may allow a patient leeway to open or close their mouth by a limited amount when the appliance is being worn.

Two geometries are equal if their shape and location are the same within a reasonable tolerance, e.g. when the difference between two geometries is unlikely to have a clinical effect. Thus, for two MRAs a 5-nanometer difference in one dimension of their geometries is unlikely to have clinical consequences, whereas differences on the order of a millimeter may be significant in the anterior/posterior direction (but less so in the open/close direction). Two geometries are different, or, more formally, "substantially different," when the difference between them exceeds the reasonable tolerance. Comparing geometries between different classes of appliances, e.g. an MRA vs. a tongue-retaining device, is more complicated.

Adjustable appliances may, by definition, assume a plurality of configurations, though only one at a time. If each configuration constrains the position of oral structures of interest differently, each configuration of an adjustable appliance will be associated with a different geometry. By assuming only one configuration at a time, adjustable appliances are therefore associated with only one geometry at a time. Thus, elements of the present disclosure apply to adjustable appliances as well.

All dimensions or axes of an appliance's geometry may not be equally important. As noted, anterior displacement of the mandible (relative to a neutral mandibular position) figures in the current art related to oral appliances. Because of the importance of the anterior/posterior axis of appliance geometries, it is often convenient to refer to positions on this axis of an appliance's geometry using the term "anterior displacement." More generally, "displacement" is, herein, the length of a vector's projection onto an axis. Although displacement may refer to an arbitrary axis and axis-origin, in many cases it refers to anterior displacement from the neutral mandibular position. The verb "displace" has a more general meaning, akin to "position."

We call a plurality of oral appliances for a single patient a "set" of appliances herein. The appliances in a set are normally of the same class, e.g. MRAs or tongue-retaining devices. Furthermore, when we say a person wears an appliance and another appliance, the "and" refers to non-simultaneous wearing of the appliances.

In a preferred embodiment, appliances in a set of appliances are tailored to fit an individual patient, e.g. to fit the patient's dentition.

The present invention provides that within a set of appliances, there are at least two different geometries represented. In a preferred embodiment, this plurality of geometries is obtained by a plurality of non-adjustable appliances, each fabricated to have a different geometry. For MRA-type appliances, the major difference in geometry between the appliances will often be in the minimum anterior displacement distance. Other embodiments are possible. For example, identical adjustable appliances may be fabricated, and then be configured to have different geometries. In another embodiment, a mixture of adjustable and non-adjustable appliances may be used.

In other words, for a set of N appliances under the present invention, there are at least M geometries represented in the set of appliances, where M and N are both two or more. When non-adjustable appliances are used, M will be less than or equal to N.

In a set of appliances having $N \geqq 2$ appliances, an exemplary embodiment would include an appliance which displaces the mandible by 75% of its protrusive capability, plus a sequence of N−1 appliances that each displace the mandible by some distance D more than the preceding appliance. In one exemplary embodiment, for example, N=6 and D=0.25 mm.

All appliances in a set need not have unique geometries. Duplicate appliances with the same geometry may be desirable as spares or for logistical reasons (e.g. a patient may keep one appliance at home and a duplicate appliance in a travel kit) or for manufacturing efficiencies.

Appliances within a set of appliances may have other therapeutic properties in addition to those attributable to their geometry. For example, oral appliances have been used to deliver positive airway pressure during sleep to patients with OSDB (U.S. Pat. Nos. 5,957,133; 5,950,624; 5,884,625) and to treat sleep bruxism. There is nothing in the present invention that precludes the incorporation of such additional functions.

In a preferred embodiment, some or all of the appliances in a set of appliances are used by a patient until an appliance is found which achieves an acceptable or optimal tradeoff between efficacy and discomfort. We call this process titration. In a preferred embodiment, the appliances will initially be used in order of increasing mandibular displacement. A further characteristic of titration, which distinguishes it from mere happenstance use of multiple appliances, is that it is embarked upon under the assumption that multiple appliances will be tried by the patient under a predetermined treatment plan. We call the appliance that is finally settled upon the "end-titration appliance."

The invention additionally provides for use after titration. Methods related to the invention are further discussed later.

The present invention also provides a means to identify, without measuring-tools, appliances in a set of appliances, or aspects of the geometry associated with the appliances. We call such means an "indicator." In a preferred embodiment, all appliances in a set of appliances will be coupled to an indicator and, to the extent the appliances have different geometries, their indicators will differ.

In a preferred embodiment, the indicator is simple for the patient to mentally manipulate. For example, indicators may, but need not, include alphanumeric characters. When alphanumeric characters are used, the fewer the number of characters per indicator, the easier patients will generally find it to remember and discuss. It is also preferable that indicators are easily perceivable by the patient, e.g. if a visual indicator is used, the indicator should preferably be of sufficient size, visibility, and contrast to allow persons with presbyopia to perceive the indicator and distinguish it from other indicators in the set of appliances without spectacles under typical indoor illumination. Indicators that glow in the dark, or are otherwise perceivable in the dark, may have advantages, since sleep often occurs in a darkened environment.

Certain appliances in a set of appliances may have the same indicator, e.g. when they have the same geometries. In such a case, the indicators may be conceptualized as representing the geometry rather than the appliance itself, and there are situations where such a representation may be preferable.

This "indicators" feature of the invention appears desirable for many reasons. For example, it may allow patients and dentists (or other health care personnel) to communicate easily and unambiguously about a particular appliance or appliance geometry, rather than having to make measurements to distinguish appliances. An appliance may be referred to by its indicator, e.g. "appliance X3." Indicators may also facilitate the patient's ability to select correctly a desired appliance from a plurality of appliances. For example, a dentist may tell a patient: "Use appliance A for one week, then appliance B for a week, then appliance C for a week, then call me." In this example, the letters A, B, and C would be indicators on three different appliances.

In an exemplary embodiment, indicators are standardized between sets, e.g. with a number indicating the tenths of millimeters of anterior mandibular displacement induced by the appliance.

In a preferred embodiment, the indicators for appliances will be ordered to reflect an ordering of the associated geometries. For example, an appliance labeled "#1" might confer the least amount of anterior mandibular displacement, the appliance labeled "#2" might confer the second-least amount, etc. Such an assignment of indicators could facilitate the use of appliances and make instructions to the patient simpler. Such an assignment may also find acceptance because it has similarities to the concept of dosing well known in pharmacological prescribing.

In appliances where mandibular positioning occurs in two different axes (e.g. anterior/posterior and open/closed), indicators may be chosen to reflect displacement in each axis, e.g. indicators consisting of a letter-number pair where the letter reflects anterior/posterior displacement and the number reflects open/close displacement. Other approaches are possible.

In some situations, e.g. blinded research studies involving oral appliances of the present invention, it may be desirable for an indicator to bear no relationship to the geometry of its corresponding appliance.

Non-geometric characteristics of an appliance may be reflected in its indicator.

Indicators may be coupled with appliances in a variety of ways, including, but not limited to, permanent embossing of an alphanumeric code 122 onto an appliance 121, as shown in FIG. #1-B; color-coding an appliance or portion of an appliance; having the indicator on a tag 112 that is removably attached to the appliance 111, as shown in FIG. #1-A; embedding the indicator within the appliance; and so on.

In some embodiments, an indicator may arise at least in part from the configuration of the appliance. For example, FIG. #2 shows a portion of an exemplary appliance that could also provide an indicator function. The portion of the exemplary MRA schematically represented in FIG. #2 consists of an upper portion 210 and a lower portion 220, corresponding to appliance portions that abut a patient's upper and lower teeth, respectively. The upper portion has a male protrusion 230 and the lower portion has a plurality of numbered female receptacles 240. Indicator numbers 250 are coupled to the appliance such that they each correspond to a female receptacle. The configuration of the appliance (and, therefore, its geometry) is determined, in part, by which of the female receptacles 240 the male protrusion 230 is inserted. When the male portion is inserted in any of the female receptacles, it is possible for a human to readily ascertain, by inspection, the corresponding indicator number 250 which may then be incorporated in an indicator for that configuration of the appliance. Thus, in this example, the indicator arises at least in part from the mechanical characteristics of the appliance, out of a plurality of possible indicator numbers coupled to the appliance.

In a specific embodiment, an indicator is palpable. For example, a palpable, "tongue-readable" indicator may allow a patient to determine the particular appliance (or appliance geometry) that he or she is currently wearing without removing the appliance from the mouth. FIG. #1-C shows an appliance 131 with three protrusions 132 amenable to perception by palpation with the tongue posterior to the position of the incisor teeth. Various physical arrangements (e.g. horizontal, vertical, diagonal, triangular, etc.) and numbers of such protrusions could serve as indicators.

Indicators may also be configured such that they are recognizable by electronic hardware or other artificial means. Elements of an electronic identification-and-data-capture system are an example of an indicator that could be recognized by artificial means. A radio frequency identification (RFID) tag with an identifier code is a possible element of such a system. For example, an RFID tag could be incorporated into each appliance in a set of appliances, with the tag containing information describing the appliance.

There is nothing in the invention to exclude an indicator that is recognizable both by humans and by artificial means, or by a human in concert with artificial means. Nor is there anything in the invention to exclude a plurality of indicators on a particular appliance. When an appliance has a plurality of indicators, some may be recognizable by humans and some may not, and some may be recognizable by artificial means and some may not.

Indicators that are recognized by an artificial recognition means may have advantages in several situations. A patient may be incapable of, or inaccurate in, recognizing indicators, e.g. a patient with dementia. An artificial recognition means could provide a data recording, monitoring, or notification means with a reference to an indicator, so that a message could be passed to the patient or caregiver if an improper appliance were being worn. In research settings it may be desirable to have an artificial recognition means identify appliances, while leaving the subject unaware of indicators and appliance identity.

In an exemplary embodiment, an artificial recognition means is coupled to a means for assessing sleep breathing. For example, a portion of the artificial recognition means could occupy the same housing occupied by a pre-tracheal sensor functioning in the diagnostic assessment of sleep breathing (see, for example, U.S. patent application Ser. No. 10/721,115). In an exemplary embodiment, an artificial recognition means in such a housing is an RFID reader that obtains information from an RFID tag in the appliance in the patient's mouth. In an exemplary embodiment, an artificial recognition means is additionally programmed with a treatment plan, or communicates with some component having access to the treatment plan, thereby permitting the correctness (according to the treatment plan) of the worn appliance to be determined and, possibly, communicated to a notification component.

Once fabricated, a set of appliances will normally need to be transmitted to a patient. Once the patient has the appliances, they will normally need to be stored when not being worn. In both cases, placing one or more appliances within one or more enclosures may be convenient. An enclosure may be, but is not limited to, a box or a sac. The enclosure may be mailable, which is to say it can be coupled to a written shipping address (or code) and it can be packed with one or more appliances in such a way that the appliance(s) are not at unreasonable risk of damage from the physical forces associated with shipping. An enclosure may be reclosable.

Other components of the invention may be usefully coupled to the enclosure, including, but not limited to, instructions-for-use, elements of the treatment plan, appliance indicator(s), means to facilitate use of appliances (e.g. a calendrical means), or a means to assess use of the invention (e.g. a diary means or an electronic use-assessment means, which could also be coupled to appliances).

In some embodiments, the enclosure may serve other purposes. For example, an enclosure may also form part of a means to clean one or more appliances, e.g. by supplying a container to hold liquid cleaning agent, into which one or more appliances are placed to soak.

Appliances from a set of appliances are typically worn one at a time during periods of time associated with sleep periods. Thus, during the daytime, a patient generally does not wear an appliance unless sleep is planned. In some cases, however, it may be helpful for the patient to wear orthodontic aligners (e.g. those described in U.S. Pat. Nos. 5,975,893 and 6,554,611) during wakefulness to counteract any tendency of the oral appliances to move teeth during sleep. Tooth movement (leading to occlusal change) is generally an undesirable possible side effect of oral appliance therapy for OSDB (Ferguson. Clin Chest Medicine. 2003; 24:355-364). Patients may be instructed to perform certain jaw motions or jaw exercises to reduce other effects of the sleep appliances.

In a preferred embodiment, a patient would be provided with a set of appliances and a treatment plan guiding the use of the appliances. In an exemplary embodiment, the treatment plan is in a readable form, including, but not limited to a hardcopy form (e.g. printed) or an electronic form (e.g. as viewed on a computer monitor or personal digital assistant). The treatment plan may refer to two or more appliances in the set of appliances provided to the patient. The treatment plan may refer to an appliance by referring to an indicator coupled to the appliance. The patient may also be provided with instructions-for-use that may or may not be in the same form as the treatment plan. The treatment plan may be provided to the patient's caretaker or other interested party.

Herein we distinguish a treatment plan from instructions-for-use. Instructions-for-use teach the use of a single appliance, e.g. "put the appliance in your mouth," or "keep the appliance clean." A treatment plan makes reference to the sequential use of a plurality of appliances. Instructions given to a patient may include elements of instructions-for-use, elements of a treatment plan, or both.

A variety of treatment plans are possible including, but not limited to, titration with one set of appliances, titration with two or more sets of appliances, and long-term use. Persons familiar with the art will understand that additional or alternative classes of treatment plans are possible. A treatment plan may be altered, even after treatment has begun.

In a preferred embodiment, titration of oral appliances for the treatment of OSDB uses information about the degree of OSDB that is present in the patient at various times and under various conditions. It is seen, therefore, that a convenient and accurate means of assessing OSDB is desirable.

OSDB may be assessed in several ways. It may be assessed by a patient, e.g. according to the degree of OSDB symptoms or sleep quality the patient experiences. OSDB may be assessed by observers, e.g. the patient's bed-partner who hears some degree of snoring or witnesses apneas. OSDB may be assessed by artificial means, such as polysomnography, oximetry, and those described in U.S. Pat. Nos. 5,671,733; 5,782,240; 5,879,313; 5,961,447; 6,045,514; 4,982,738; 5,275,159; 6,120,441; 6,290,654; 6,213,955; 6,171,258; 5,797,852; 6,142,950; 6,306,088; 6,319,205; 6,322,515; and U.S. patent application Ser. No. 040,937, for example. Combinations of techniques may be used. Measurement of respiratory rate, body movement, and/or oronasal air flow may be useful in some cases. Other methods are possible. As noted above, an artificial means for assessing OSDB may be coupled to an artificial means for recognizing appliance indicators.

In an exemplary embodiment, titration precedes a phase of (stable) long-term use of appliance(s) having a single geometry. Titration may generally be conceptualized as a process to correlate a plurality of appliance geometries with: assessments of discomfort, or one or more features of the patient's OSDB, or both. With this correlation in hand, a decision about the geometry of a long-term appliance (if any) can be made rationally.

In an exemplary embodiment of a titration using a set of appliances, the N appliances in the set are ranked from 1 to N, according to the minimum mandibular displacement induced by each appliance, and the rank number is the indicator for each appliance. For simplicity, we assume the appliances in the set displace the mandible in a uniform direction; appliances with more complicated displacements may require more complicated ranking functions. Thus, appliance 1 corresponds to the appliance associated with the least mandibular displacement and appliance N corresponds to the appliance associated with the greatest mandibular displacement. In such an embodiment, an exemplary treatment plan would direct that the patient wear appliance 1 until some endpoint is reached, then wear appliance 2 until some endpoint is reached, and, assuming $N \geq 3$, so on for appliances 3 to N or until titration was completed.

FIG. #3 is a flowchart for an exemplary titration treatment plan. Titration begins 310 with a patient selecting the initial appliance from a set of N appliances referenced by the treatment plan, where the appliances are ranked and indicated by mandibular displacement as described above. This selected appliance is now the "current appliance," or, synonymously, "appliance M," where M is an integer from 1 to N, inclusive. After the patient wears the current appliance (step 320), an optional assessment (step 330) is made of the effects of wearing the appliance. This assessment could include the degree of discomfort associated with wearing the current appliance, the therapeutic effectiveness of wearing the current appliance (as determined, for example, from assessing OSDB severity during wear of the appliance), and so on. The assessment may be made after each night of wear, after some larger number of nights of wear, or even after less than a night's wear (e.g. a test wearing). The treatment plan may specify the interval for such assessments, but it in many cases the patient will make at least an informal assessment after each wearing.

After wearing the current appliance (step 320), a decision 340 can be made whether to continue titration. This decision can be based on a number of factors, including but not limited to the effects of wearing the current appliance as determined in step 330, the availability of an appliance with a greater mandibular displacement, and the like.

In the event titration is continued, it can be asked (step 350) whether the current appliance (appliance M) should continue to be worn, or whether an appliance with the next greater degree of mandibular displacement (appliance M+1) should be worn. This decision 350 can be based, for example, on the number of nights that appliance M has been worn, the degree of patient discomfort associated with wearing appliance M, the number of discomfort-free nights the patient has had wearing appliance M, and so on. If the decision 350 is to continue wearing the current appliance, then the cycle repeats (starting with step 320) when the patient next wears the current appliance. If the decision 350 is to switch to appliance M+1 (i.e. the appliance with the next greater degree of mandibular advancement than the current appliance), then appliance M+1 is designated the current appliance, as indicated by the increment in M in step 360. The cycle then repeats (starting with step 320), with the newly designated current appliance.

As noted above, a variety of factors could be used to decide that the titration phase should be ended. For example, intractable patient discomfort with appliance M could precipitate the end of the titration phase, based on a decision that continued attempts to use appliance M are not warranted and that appliances with greater degrees of mandibular displacement (i.e. appliances M+1 to N, where M<N) are likely to also be associated with unacceptable levels of discomfort. As a further example, it may be determined that appliance M achieves the desired therapeutic effect, and there is therefore no need to try other appliances. As a further example, all appliances, 1 to N, in the set of appliances may have been repeatedly worn by the patient, with the result that there are no appliances in the set of appliances left to try. In such a situation, a treatment failure may be declared (see below).

At the end of the titration phase, the end-titration appliance is determined 370. One possible heuristic to guide the selection might be: "Pick the appliance that (a) has the smallest degree of mandibular displacement achieving the desired therapeutic effect, and (b) is well-tolerated by the patient." As an example, consider a situation where the titration showed that appliance M lowered the patient's apnea-hypopnea index (AHI) to 2/hr but was associated with significant patient discomfort, while appliance M−1 (i.e. the appliance with the greatest mandibular displacement that is less than the mandibular displacement of appliance M) lowered the patient's apnea-hypopnea index to 3/hr and was well-tolerated by the patient. If the desirable therapeutic effect in this example is to lower the patient's AHI to less than 5/hr, then appliance M−1 may be chosen as the end-titration appliance, because it achieved that and was well-tolerated by the patient.

In cases where an adequate therapeutic effect is not achieved with any of the appliances that the patient can tolerate, a treatment failure may be declared (not shown in FIG. #3). In such a situation a new set of appliances may be ordered and titration initiated with the new appliances. Such a re-titration is most likely to be effective if the new appliances have different geometries than the original set of appliances, or if the new appliances differ in some other significant way from the appliances in the original set of appliances, e.g. the new appliances lack a specific feature that in the original appliances was causing discomfort to the patient.

An exemplary titration treatment plan (co-mingled with instructions-for-use) given to the patient might be: "A goal of treatment is to find an oral appliance that is both comfortable to wear and effectively treats your sleep breathing problem. You have been given a set of oral appliances. The appliances are numbered 1 through 5. You will wear an appliance each night when you sleep. You will choose which appliance to wear based on the schedule below. Whichever appliance you wear, put it in your mouth before you go to bed, and remove it from your mouth when you get up to start your day. You should wear your appliances according to the following schedule: Appliance #1: Wear it each night for a month. Appliance #2: Wear it each night for two weeks. Appliance #3: Wear it each night for two weeks. Appliance #4: Wear it each night for two weeks. Appliance #5: Wear it each night for a week, then telephone your dentist. The appliances are built to be comfortable to wear, and the schedule is built to give you time to get used to each of the appliances. Despite this, some appliances may be uncomfortable. Discomfort usually decreases over time, but if an appliance is uncomfortable after two consecutive nights of wear, call your dentist. If an appliance causes bleeding, remove the appliance and call your dentist the next morning."

In the example treatment plan above, time is the predominant factor determining when a change is made from one appliance to another. Although a precise time was used in the example, a time range, e.g. "one to two weeks," may also be used. As noted earlier, other factors may be used to determine when to change from one appliance to another; these factors may be reflected in the treatment plan. Such factors include, but are not limited to: (1) the presence or degree of adverse consequences of appliance wear (e.g. discomfort, bleeding, gingival or other dental effects), (2) assessment(s) of the patient's breathing (e.g. subjective assessments such as a bedpartner's perception of snoring by the patient, or objective assessments of the patient's breathing during sleep), or (3) assessment(s) of consequences of sleep-disordered breathing in the patient (e.g. assessment of symptom(s) and/or sign(s) of sleep-disordered breathing, including hypertension, heart failure, nocturia, cognitive effects, and the like), or (4) assessment(s) of whether the patient has been using the appliances in proper accord with the treatment plan.

The treatment plan may be formulated to maximize simplicity. In the example above, 3 of the 5 appliances are scheduled to be worn for two weeks during the titration phase. The schedule could be simplified by making all wear-periods the same. Dentists and other health care professionals will likely appreciate this flexibility in patients with limited self-care abilities, in whom overall treatment success may result more from patient understanding and compliance than from optimal scheduling.

In a preferred embodiment, the treatment plan is presented to the patient before beginning wear of an appliance from the set of appliances. The treatment plan may include adjuncts, such as a calendar to remind or assist the patient in determining which appliance should be worn on a particular date. The calendar may be annotated with references to a specific appliance, to a specific action (e.g. "Call your dentist's office today and give a progress report"), to decisions, to questions, and the like. In cases where the patient needs assistance with care, the calendar may be given to a relative, a friend, or other caretaker. The calendar may be paper-based or electronic, e.g. implemented on a personal digital assistant. The calendar may be generated by a human or by a computer or other device.

In an alternative embodiment, the specifics of a treatment plan may be presented to a patient over time. For example, after awakening each morning during the titration process, the patient could call a telephone interactive response system, and be prompted to enter information about recent appliance use, e.g. the current appliance's indicator, the degree of discomfort associated with wearing the appliance, the degree of OSDB symptoms, the bed-partner's report of snoring, etc. The response system could use an algorithm of arbitrary complexity, possibly tailored to the individual patient and appliance set, to determine the next treatment(s) to be used in the treatment plan. The patient could then be so informed on the telephone, or later. Thus, when the treatment plan itself may be too complicated to present fully to the patient, instructions on how to access an interface to the treatment plan may be given instead.

FIG. #4 shows a flowchart for a possible treatment plan in which multiple treatment steps (450, 460, 470, 480) are possible after an assessment 430 of the effect of wearing an oral appliance. The treatment plan begins by selecting an appliance $M_0$ from a set of appliances for the patient to wear initially (step 410). As in FIG. 3, the currently worn appliance is referred to as appliance M (420). In this embodiment, the assessment 430 has been structured to provide information along two axes: effectiveness and comfort of appliance M. Given the larger number of possible treatment steps in this embodiment, the step of deciding on a particular treatment step (440) may be relatively complicated (see FIG. #5 and discussion below). Possible treatment steps include ending titration successfully 450 or declaring a treatment failure 460 with the current set of oral appliances. Another possible treatment step 470 is to add or change a treatment modality other than oral appliances, for example, instituting positional therapy with a tennis ball sewn to the patient's pajama top, using a Breathe-Right® strip to improve nasal airflow, using a medication to suppress rapid-eye movement sleep, etc. Another possible treatment step is to select a different appliance to wear 480, one that might have a greater mandibular displacement than the current appliance (e.g. "M←M+1") or one having less mandibular displacement than the current appliance (e.g. "M←M−1"). There may be cases in which performing more than one treatment step after an assessment 430 may be advisable.

FIG. #5 shows an exemplary embodiment of deciding on a treatment step (akin to step 440). In this embodiment, the decision is based on two inputs: the degree of discomfort associated with wearing appliance M, and the degree of effectiveness with which appliance M treats the patient's sleep breathing problem. The degree of discomfort is described as 0 (no discomfort), 1 (tolerable discomfort), or 2 (intolerable discomfort). The degree of effectiveness is described as 0 (not effective), 1 (marginally effective), 2 (mostly effective), or 3 (completely effective). For a given level of discomfort and effectiveness for a given oral appliance M, FIG. #5 shows what treatment(s) to perform next. It can be seen that the decision table is sufficiently complex, and the inputs sufficiently simple, that an adjunct such as the interactive telephone system mentioned above may be beneficial.

A predetermined treatment plan referencing a plurality of appliances is present in several embodiments of the present invention. A predetermined treatment plan can be helpful by setting the patient's expectations appropriately, enhancing control of the clinical process, enhancing the range of appliance treatment options, and permitting certain manufacturing and logistical efficiencies.

Titration of oral appliance therapy for OSDB, when performed outside of a sleep laboratory, generally proceeds over days and weeks in the current art. Features of the present invention, however, could enable more rapid titration, e.g. in one night in some cases.

For titration to occur in one night, it follows that adjustments to the patient's oral appliance(s) may need to be made during the night. It is well known that some persons encounter difficulty concentrating immediately after being awakened from sleep. Thus, patients who have just been awakened from sleep may find it difficult to concentrate to the degree required to adjust an appliance in the existing art, since concentration is needed for some adjustment procedures.

A feature of the present invention, however, is that changes in mandibular positioning may be accomplished in many cases without demanding significant concentration from the patient. For example, to increase the amount of mandibular displacement during an awakening from a sleep period, the patient need only remove the current appliance from his or her mouth, and select and insert a different appliance having a greater displacement. It is seen that this sequence of steps requires relatively little concentration from the patient, suggesting that many patients will be able to perform multiple titration steps during the period of time associated with a sleep period, albeit an interrupted sleep period. Demands on the patient may be further reduced by devices that prompt the patient on what action to take, e.g. "Insert appliance #3."

In a preferred embodiment, the titration process includes a monitoring means coupled to a notification means. The monitoring means may, for example, collect and act upon data related to OSDB severity in a patient. The notification means alerts the patient to various situations at various times. Because the patient may have been sleeping or attempting to sleep at such times, a notification means may use one or more methods of capturing the patient's attention, including, but not limited to, delivering (or causing to deliver) a noise to the patient, a shock to the patient, a vibration to the patient, combinations of the above, and so on. The patient's bedpartner or caretaker may be notified in some cases.

FIG. #6 summarizes a preferred embodiment for operation of the monitoring means. The monitoring means is first configured with a plurality of operating parameters 610, e.g. element(s) of a treatment plan, descriptors of the set of appliances used by the patient, criteria for notifying the patient of certain events, and the like. A variety of other parameters may be loaded, e.g. the name of the patient.

Monitoring of patient-related physiological and environmental data 620 may begin automatically (e.g. at a predetermined time or upon detection of a certain set of circumstances such as appliance wear) or with input from the patient (e.g. pressing a button). In an exemplary embodiment, the monitoring means is able to recognize an indicator of the appliance worn by the patient. After reading the indicator, the monitoring means may determine 640 whether the appliance being worn is the appliance that should be worn, according to the operating parameters loaded in step 610. If the correct appliance is not being worn, the monitoring means formulates a message 680 for the patient, then passes a specification of the message to the notification means 695 (see below). The message may be symbolic, e.g. illumination of a certain light emitting diode; textual, e.g. the string "wrong appliance;" etc.

If the correct appliance is being worn, or if the monitoring means does not have the capability to determine the indicator being worn, processing of incoming data may begin 650. Assuming the monitoring means has not been deactivated 660 (e.g. deactivating by pressing an "off" button), a determination is made 670, after an appropriate amount of data have been processed, as to whether the data meet criteria for notifying the patient. For example, a reasonable notification criterion might be: "if the patient has had more than 5 apneas or hypopneas in the preceding 60 minutes, notify the patient to switch to the next appliance specified by the treatment plan." The corresponding message that might be delivered to the patient in such a situation might be "Change to appliance #4." After formulation of the message to be delivered to the patient 690, the message specification for the message is passed to the notification means 695 for delivery to the patient.

It is seen from the description above that the monitoring means, in a preferred embodiment, should be capable of determining the presence or absence of OSDB in near-real time, so that notification messages may be generated and delivered promptly. It may, therefore, incorporate a means to assess OSDB.

In a preferred embodiment the monitoring means has access to information about the position of the patient's body (with respect to gravity) at substantially the same time it has access to information about the dynamics of the patient's ventilation. Body-position information is often valuable in this context because the effectiveness of an oral appliance may vary according to body position. For example, in some cases, OSDB is more severe when a patient is sleeping in the supine position. When assessments of OSDB are performed over relatively short periods of time (e.g. less than several hours during a night's sleep), it may be important to know that a patient has not yet slept in the supine position (for example) with a particular appliance. In such an example, the appliance may not yet be considered "acceptable" unless it has been used by the patient over a period of time in the position where OSDB is generally the most severe. Thus, not only may it be helpful to have the monitoring means determine when OSDB is still present, it may also be helpful to have the monitoring means determine that sufficient data have been collected to reasonably exclude the presence of OSDB. (Similar considerations may apply to certain sleep stages.)

Thus, in an exemplary embodiment, the patient sleeps with a sensor for the assessment of OSDB that detects both tracheal sound and body position (as described in U.S. patent application Ser. No. 10/721,115). It will be apparent to those skilled in the art that other instrumentation arrangements for the assessment of sleep breathing are possible, examples of which were noted earlier.

In a preferred embodiment, the notification means 695 is an audio speaker. The messages formulated in steps 680, 690, or elsewhere may therefore be output so the patient can hear them. Text-to-speech software, known to persons skilled in the art, may be used to facilitate the output. Various techniques to get the patient's attention, such as repeating messages at louder volumes, or vocalizing the patient's first name, may be employed. In many cases it will be desirable for the invention to have a means for the patient to stop notification. Alternatively, the monitoring means may detect a change in conditions (e.g. the patient is now wearing a different appliance) and cease notification as a result. After notification ceases, control may revert to the monitoring means, for example at step 630.

Repeated assessments, notifications, and appliances may enable a patient to perform several titration step changes during a night (or other period of time associated with a sleep period). In some cases, a patient may be able to complete titration in one night.

One plausible method to minimize the expense associated with the present invention is to minimize the number of appliances fabricated and delivered to the patient. Too few appliances, however, may have undesirable consequences. For example, displacements may be spaced too far apart, so that one appliance is sub-therapeutic and the appliance with the next-greatest degree of displacement is uncomfortable. An alternative approach to minimizing the number of appliances is to fabricate and deliver them as needed, but there is expense associated with such an approach as well.

A middle ground is to use two sets of appliances, wherein the appliances in the first set have displacements that are spaced relatively widely and the appliances in the second set have displacements that are spaced relatively narrowly. The patient's ideal displacement may be approximated by the first set of appliances, and more precisely determined afterwards with the second set of appliances. The second set of appliances is fabricated to have displacements in a range derived from those appliances from the first set that worked the best with the patient.

In an exemplary embodiment, titration with the first set would identify two appliances, one being sub-therapeutic but comfortable and the other therapeutic but uncomfortable. The second set of appliances could then be fabricated, with displacements in this second set spaced between the displacements of the two appliances identified in the first set, and delivered to the patient. Titration with the second set of appliances (possibly including the two appliances identified from the first set as well) would then determine the long-term appliance geometry for the patient.

A second set of appliances would not be necessary if an appliance in the first set were both therapeutic and comfortable.

Ivanhoe and Attanasio (Dent Clin North Am. 2001 October; 45(4):733-58.) note that success often accompanies empirically choosing an appliance with a displacement of 70-75% of the maximum mandibular protrusion a patient can obtain relative to maximum retrusion. Thus, it seems reasonable for the initial set of appliances to have detailed displacement resolution at or near this amount. The intervals between displacements in a set of appliances need not be identical.

The present invention could be used in association with an adjustable appliance, wherein the adjustable appliance substitutes in function for the first set of appliances. In this embodiment, the adjustable appliance need not be durable, since it will be used only for the short period of time it takes to complete the initial titration.

In some cases it may be preferable to deliver a small number of appliances separately to the patient over time, rather than in large sets. For example, FIG. #5 includes a treatment step in which the patient is asked to wear a tolerably uncomfortable appliance for a week before wearing a different appliance. Should a treatment plan include one or more situations in which there is advance warning that a certain appliance is required, it would be possible to defer manufacture and/or shipping of the certain appliance until the patient has progressed to a point in the treatment plan where it is certain (or above some probability threshold) that the appliance will be needed. Manufacture of appliances at different times is more likely to be economically feasible if the manufacturing occurs from the same initial mechanical description of the patient's oral structures.

Once an end-titration appliance has been chosen, this appliance may thereafter be recommended for chronic night-time (i.e. sleep-time) use by the patient. Alternatively, a geometry associated with the end-titration appliance may be used to fabricate a "long-term" appliance with a similar geometry but having different non-geometric features.

For example, the appliances used in titration might be made less durable in order to reduce cost. In such a case, once the end-titration appliance is determined, a higher cost, more durable appliance having the same geometry as the end-titration appliance can be fabricated for long-term use by the patient.

A long-term appliance having no change in geometry over time will likely be adequate to manage some patients with OSDB. However, the clinical state of some patients will change over time. Such a change may alter the effectiveness of a given appliance geometry over time.

For example, some patients may gain weight or become hypothyroid. Over generally shorter periods of time, a patient may imbibe alcoholic beverages, may become partially sleep deprived, may begin taking certain medications, or may develop nasal congestion. All of these factors, and others as well, may unfavorably influence OSDB in some patients, rendering treatment with the long-term appliance less effective.

Conversely, weight loss, treatment of hypothyroidism, lessening of alcohol or cigarette use, or discontinuation of certain medications (e.g. certain sedatives) may occur. These factors, as well as others, may favorably influence OSDB in some patients, rendering treatment with the long-term appliance excessive.

Issues related to comfort with a long-term appliance may arise, e.g. if a patient develops dysfunction of a temporomandibular joint.

Thus, it is seen that various events may re-initiate the search for an appliance (or appliance geometry) best suited for the patient, a process we call "re-titration." A plurality of treatment plans are possible for re-titration; FIG. #7 shows an example. FIG. #7 assumes the patient has been wearing an appliance M (710). (This is not required for all re-titrations, e.g. the patient may be non-compliant with appliance therapy).

In cases where an alteration in clinical state or an alteration in appliance effectiveness is suspected, it may be desirable to assess the degree of OSDB using an assessment means, with the decision to pursue re-titration dependent, at least in part, on the results. In some other cases, just the suspicion of a change 720 may be sufficient to initiate re-titration. In yet other cases, assessments of OSDB may be performed in a surveillance mode, i.e. without specific cause, in order to detect changes in effectiveness of the long-term appliance that might otherwise escape notice.

In cases where improvement of OSDB is suspected or documented, it may be reasonable to attempt down-titration, i.e. a lesser degree of mandibular displacement may be required than previously as in steps 730 and 750. In some situations, patients may be able to dispense with oral appliance therapy. In cases where worsening of OSDB is suspected or documented, it may be reasonable to attempt up-titration as in steps 730 and 740. In a preferred embodiment, a change in the appliance worn leads to assessment of airway function and adverse effects of the appliance 760, followed by a decision 770 on whether the patient's clinical state is acceptable with the new appliance.

As mentioned, some factors influencing OSDB may occur relatively acutely. In such cases, deviation from the long-term appliance may be beneficial. For example, if a patient has consumed alcohol, he or she may wish, on that night, to use an appliance imparting greater mandibular displacement than the long-term appliance. This is an example where the appliance worn is changed without an assessment. Such a change may be based on past experience (in which assessments were made after consuming alcohol) or based on a knowledge base (correlating alcohol intake with OSDB severity). In some cases a patient's bed-partner may notice (or be disturbed by) uncharacteristic snoring from the patient, despite the patient wearing the long-term appliance. The patient may be prompted to awaken and insert an appliance with a greater displacement.

In an embodiment of the present invention, a full set of appliances is manufactured and transmitted to a patient in one shipment. This approach may be associated with manufacturing and shipping efficiencies. In an alternate embodiment, all appliances in a set of appliances may not be transmitted to the patient in one shipment, e.g. one or more appliances of a set of appliances, coupled with a treatment plan that refers to two or more of the appliances in the set, may be transmitted in one shipment, with other appliances to follow. In this embodiment the treatment plan possibly mentions or alludes to a fact that the two or more appliances have different geometries (although not necessarily in those words). Shipping less than the full set of appliances may incur lower overall costs if the cost of manufacturing appliances is high or if closer control of the patient's appliance use is desired.

When appliances are tailored to a patient's dentition, information about the mechanical structure of the patient's dentition is normally received by one or more entities involved in the fabrication of the appliances. This information often includes a description of the shape of the teeth and a description of the relative position between mandible and maxilla. Additional information, e.g. the maximal protrusion of the mandible, the extent of the gums, or information related to the desired geometries of the appliances may also be included.

Such mechanical information may be captured by taking a casting (sometimes called "an impression") of the patient's dentition. Appliances may then be constructed on the basis of the casting. Alternatively, appliances could be tailored to a patient by having the patient perform a "tailoring maneuver," e.g. incorporating a deformable material into an appliance and having the patient bite down on the deformable material in order to provide a custom fit to the patient's dentition. Such materials are known to persons with ordinary skill in the art, including materials that are deformable only under certain conditions, e.g. elevated temperatures.

Alternatively, appliances may be tailored to fit an individual patient by using information obtained during a scan of the patient's oral cavity and associated structures. For example, information collected during magnetic resonance imaging or other imaging of the head may be used to develop a three-dimensional representation of the patient's dentition in a computer memory, and appliances may be fabricated on the basis of that representation. Other imaging modalities (e.g. computerized tomographic X-ray imaging) are known to persons with ordinary skill in the art.

When a casting is made, the cast may be physically transmitted to the manufacturer. In general, however, electronic communication will often be more rapid than such physical transmissions. Thus, there may be advantages associated with transmitting mechanical information electronically, e.g. from one computer memory to another.

In some cases, the mechanical information provided to the manufacturer may be incomplete or inadequate. For example, an appliance may need to be modified ("re-worked") in order to give the patient a comfortable fit, e.g. if information about the extent of the gums, relative to the teeth, is not provided and an appliance is fabricated that painfully impinges on the gum. When an appliance is transmitted to the patient, it would appear desirable to minimize the amount of re-work it might later need.

One approach to minimizing re-work is to obtain initially as complete a description of the patient's oral cavity as practical and possible.

Another approach is to make a first appliance for a patient based on mechanical information obtained, then test-fit the appliance in the patient, then communicate descriptions of any necessary rework back to the manufacturer for incorporation into future appliances for the patient.

An exemplary embodiment of this approach is a computer station in which the dentist indicates, with light pen, graphics tablet, mouse, or other 2-dimensional or 3-dimensional input device, the location and nature of rework required on an appliance to obtain a satisfactory fit for a patient. The computer then transmits this rework information to the manufacturer, where the information is merged with pre-existing mechanical information concerning the patient's oral cavity and/or previous appliance(s). Subsequently, appliance(s) may be manufactured for the patient with the rework modifications already present, reducing the odds that rework of the same type would be needed on the newly manufactured appliances.

In an exemplary embodiment, an oral appliance that has been subjected to rework is placed in a computer-connected apparatus that allows 3-dimensional localization of points in space. A dentist may indicate a particular point (or region) of the appliance with an input device, and supply the computer with information about rework performed in the vicinity of the point or region. The rework information may be entered on a computer keyboard or with other computer input devices familiar to those with knowledge of the art.

In such an embodiment, it would be desirable for the coordinates of the point (or region) to be expressed according to a frame of reference that could be applied to the appliance as well. A common frame of reference would allow localization of the point (or region) with respect to the appliance. For example, a 3-d scanner could determine the shape of the appliance and its surface boundaries in an arbitrary frame of reference, and the indicated point (or region) could be expressed in the same frame of reference; other approaches are possible. Certain markings or structures on or in the appliance may serve as the basis for establishing a coordinate system.

In a preferred embodiment, a reworked appliance is 3-dimensionally scanned by a computer-connected apparatus, providing a digital representation of at least the appliance's shape. The digital representation of the reworked appliance is compared to a digital representation of the appliance before rework (again requiring one or more common reference frames), allowing the reworking to be identified, isolated, and represented digitally. The reworking would then be applied to subsequently manufactured appliance(s).

Alternatively, the representation of a reworked appliance could itself be used as a basis for manufacturing subsequent appliance(s), without identifying, isolating, or representing the rework specifically.

It is seen, therefore, that there are advantages to keeping information about a patient's oral cavity in a digital system, as it will be simpler, in most cases, to consolidate newly-gained information with older information, as compared to a mold or casting.

Certain efficiencies under the invention may result when appliances are manufactured synchronously. In an exemplary embodiment, a plurality of oral appliances, wherein at least two of them have substantially different geometries, may be said to be manufactured synchronously when any of: (a) they are manufactured close together in time, e.g. less than 48 hours, (b) there was no feedback to the manufacturing process between the time of a first appliance's fabrication and the time of a second appliance's fabrication that altered the planned geometry of the second appliance, or (c) they are transmitted to the patient, unused, simultaneously or in a common enclosure or in a common shipment. Additional embodiments of synchronous manufacture are possible, and there is a similar embodiment for a configurable appliance (i.e. an appliance whose geometry is determined, at least in part, by one or more configuration steps), if the words "configuration" and "configured" replace "manufacture" and "manufactured" in the embodiment just disclosed. In some cases, the appliances may have been tailored to the patient substantially before the configuration step(s).

The present invention has many potential advantages. When a plurality of mechanically simple, e.g. non-adjustable, appliances is used per the present invention, both the mechanical complexity and the manufacturing expense may be lowered compared with adjustable appliances. Yet, advantages usually associated with adjustability would still be available to patient and dentist (and possibly other health care professionals), by virtue of the different geometries represented by the plurality of simple appliances. Additionally, the present invention need not employ special tools or parts to adjust appliances.

A further advantage associated with using inexpensive appliances in the present invention is logistical flexibility for patients. For example, a patient can, for a relatively low cost, order multiple copies of the end-titration appliance, e.g. he or she can keep one appliance at home next to the bed, pack another appliance in his or her travel kit, keep another appliance at a relative's house that is frequently visited, and keep another appliance as a spare.

A further advantage of the present invention is the potentially smaller amount of time required for a dentist to manage a patient's care compared to other methods of oral appliance therapy. For example, patients need not return to the dentist's office to have an appliance adjusted; instead, adjusting a patient's mandibular position using the present invention can be done over the telephone with a simple sentence such as "Switch from appliance #2 to appliance #3." As a further example, using non-adjustable appliances in the present invention means that, in principle, there will be no need for a patient to visit a dentist upon completion of titration in order to have an appliance "locked in" to a final position. Yet, the dentist does not sacrifice flexibility, because of the plurality of appliances available for him or her to treat the patient.

Another advantage of the present invention is the potential simplicity of instructions that a patient will need upon initiating treatment. Examples of possible instructions have already been given. Such instructions are often simpler than instructing the patient on the mechanics of adjusting an adjustable appliance, or having the patient come in for office visits during the titration process. Indeed, instructions for use of the present invention can approach the simplicity of pharmacological titration instructions. For example, a physician might instruct a medicine-taking patient as follows: "Take one pill a day for two weeks, then two pills a day for two weeks." A similar instruction given to a patient that could apply to the present invention might be: "Wear appliance #1 at night for two weeks, then appliance #2 for two weeks."

Using the present invention, even relatively complicated portions of treatment plans may be described with simple patient instructions, e.g. "Wear each appliance for two weeks after your discomfort with it vanishes, then advance to the next appliance in sequence and repeat" or, after brief coaching on pain scales, "Wear each appliance for two weeks after your discomfort with it drops to 3-out-of-10 or less, then advance to the next appliance in sequence and repeat."

There are other potential advantages. Because the time needed from a dentist may be reduced and because instructions to patients are largely free of the need for detailed dental knowledge, once the oral appliances of the present invention are delivered to a patient, it becomes reasonable for a non-dentist physician to manage the patient's oral appliance therapy. (Most physicians, of course, are not dentists.) In such a case, attention might be needed from the dentist only in anomalous situations and for routine long-term follow-up of the patient's dentition and oral health.

A novel feature of the present invention is that it potentially brings a simple and reliable dosing method to oral appliance therapy for OSDB. The importance of dosing is illustrated by the familiar model of dosing in the pharmacological treatment of hypertension: if the blood pressure of a patient being treated for hypertension rises to undesirable levels, the dose of the patient's anti-hypertensive medication can often be increased to bring the blood pressure back to desirable levels. The present invention allows a similar "dose" adjustment, where "dose" derives from appliance geometry. If a patient under treatment for OSDB develops, for example, new symptoms or signs of OSDB, the patient can be instructed to try an appliance providing greater mandibular displacement than the appliance the patient is currently wearing.

Similar advantages carry into situations where the proper "dose" of mandibular displacement might change more rapidly, for example, after alcohol consumption, when sleep deprived, during a transient illness, etc.

It should be noted that the above sequence of steps is merely illustrative. Any of the above steps can also be separated or be combined, depending upon the embodiment. In some cases, the steps can also be changed in order without limiting the scope of the invention claimed herein. One of ordinary skill in the art would recognize many other variations, modifications, and alternatives. It is also understood that the examples and embodiments described herein are for illustrative purposes only and that various modifications or changes in light thereof will be suggested to persons skilled in the art and are to be included within the spirit and purview of this document.

What is claimed is:

1. A method for fabricating a set of appliances for treating a patient having obstructive sleep disordered breathing, the method comprising:

obtaining information associated with a mechanical description of the patient's oral cavity;

manufacturing, based on the information associated with the mechanical description, a set of appliances being adapted to displace a mandible of the patient by a plurality of predetermined geometries relative to a maxilla of the patient, the set of appliances comprising a first appliance being adapted to displace the mandible by a first predetermined geometry relative to the maxilla, at least a second appliance adapted to displace the mandible by a second predetermined geometry relative to the maxilla, and the first predetermined geometry is substantially different from the second predetermined geometry;

packaging the set of appliances; and transmitting the set of appliances including the first appliance and at least the second appliance to the patient.

2. The method of claim 1 wherein manufacturing of the first appliance and manufacturing of at least the second appliance occur within 48 hours of each other.

3. The method of claim 1 wherein no additional information associated with the mechanical description of the patient's oral cavity is obtained between the manufacturing of the first appliance and the manufacturing of at least the second appliance.

4. The method of claim 1 wherein the set of appliances is packaged within a single enclosure.

5. The method of claim 1, wherein the information associated with a mechanical description of the patient's oral cavity is obtained at a first location where the manufacturing is not performed, and is sent to at least a second location where the manufacturing is performed.

6. The method of claim 5 wherein the sending occurs electronically.

7. The method of claim 5 wherein no additional information associated with the mechanical description of the patient's oral cavity is sent between the manufacturing of the first appliance and the manufacturing of at least the second appliance.

* * * * *